(12) United States Patent
Seo et al.

(10) Patent No.: US 9,738,621 B2
(45) Date of Patent: Aug. 22, 2017

(54) MULTIFUNCTIONAL MATERIALS AND COMPOSITES

(71) Applicant: ARIZONA BOARD OF REGENTS, A BODY CORPORATE OF THE STATE OF ARIZONA ACTING FOR AND ON BEHALF OF ARIZONA STATE UNIVERSITY, Scottsdale, AZ (US)

(72) Inventors: Dong-Kyun Seo, Chandler, AZ (US); Ki-Wan Jeon, Tempe, AZ (US)

(73) Assignee: ARIZONA BOARD OF REGENTS, A BODY CORPORATE OF THE STATE OF ARIZONA ACTING FOR AND ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 132 days.

(21) Appl. No.: 14/379,021

(22) PCT Filed: Feb. 15, 2013

(86) PCT No.: PCT/US2013/026314
§ 371 (c)(1),
(2) Date: Aug. 15, 2014

(87) PCT Pub. No.: WO2013/123308
PCT Pub. Date: Aug. 22, 2013

(65) Prior Publication Data
US 2014/0371443 A1 Dec. 18, 2014

Related U.S. Application Data

(60) Provisional application No. 61/599,250, filed on Feb. 15, 2012.

(51) Int. Cl.
| | | |
|---|---|---|
| C07D 331/02 | (2006.01) | |
| C01B 19/00 | (2006.01) | |
| C01B 31/02 | (2006.01) | |
| C01B 31/04 | (2006.01) | |
| C08B 11/02 | (2006.01) | |
| C08B 11/20 | (2006.01) | |
| C08B 15/05 | (2006.01) | |
| C08L 1/08 | (2006.01) | |
| C08L 1/28 | (2006.01) | |
| B82Y 30/00 | (2011.01) | |
| B82Y 40/00 | (2011.01) | |
| C07D 345/00 | (2006.01) | |
| C08B 15/00 | (2006.01) | |
| C08L 101/06 | (2006.01) | |

(52) U.S. Cl.
CPC .......... *C07D 331/02* (2013.01); *B82Y 30/00* (2013.01); *B82Y 40/00* (2013.01); *C01B 19/00* (2013.01); *C01B 31/026* (2013.01); *C01B 31/0484* (2013.01); *C07D 345/00* (2013.01); *C08B 11/02* (2013.01); *C08B 11/20* (2013.01); *C08B 15/00* (2013.01); *C08B 15/05* (2013.01); *C08L 1/08* (2013.01); *C08L 1/28* (2013.01); *C08L 101/06* (2013.01); *Y02P 20/134* (2015.11)

(58) Field of Classification Search
CPC ... C01B 19/00; C01B 31/026; C01B 31/0484; C08B 11/02; C08B 11/20; C08B 15/05; C08B 15/00; C08L 1/08; C08L 1/28; C08L 101/06; B82Y 30/00; B82Y 40/00; C07D 331/02; C07D 345/00; C07C 49/217
USPC ................... 536/92, 56; 549/3, 90, 512, 513
See application file for complete search history.

(56) References Cited

U.S. PATENT DOCUMENTS

| | | | | |
|---|---|---|---|---|
| 3,330,787 | A * | 7/1967 | Faessinger | ............... C08B 11/04 527/311 |
| 3,346,667 | A * | 10/1967 | Firth | ....................... A01N 25/30 44/305 |
| 3,914,214 | A * | 10/1975 | Trimnell | ................. C08B 15/00 536/102 |
| 5,578,718 | A * | 11/1996 | Cook | ............... C12Y 113/11012 536/27.21 |
| 6,875,274 | B2 | 4/2005 | Wong et al. | |
| 7,670,584 | B2 | 3/2010 | Caldwell et al. | |
| 7,829,055 | B2 | 11/2010 | Lee et al. | |
| 7,892,517 | B2 | 2/2011 | Tour et al. | |
| 7,935,683 | B2 | 5/2011 | Mizu et al. | |

(Continued)

FOREIGN PATENT DOCUMENTS

| | | |
|---|---|---|
| WO | WO0015734 | 3/2000 |
| WO | WO02087871 | 11/2002 |

OTHER PUBLICATIONS

Czech et al, Phys. Stat. Sol., 2006, 243(1), 3221-3225.*

(Continued)

*Primary Examiner* — Ganapathy Krishnan
(74) *Attorney, Agent, or Firm* — Fish & Richardson P.C.

(57) ABSTRACT

Forming multifunctional materials and composites thereof includes contacting a first material having a plurality of oxygen-containing functional groups with a chalcogenide compound, and initiating a chemical reaction between the first material and the chalcogenide compound, thereby replacing oxygen in some of the oxygen-containing functional groups with chalcogen from the chalcogen-containing compound to yield a second material having chalcogen-containing functional groups and oxygen-containing functional groups. The first material is a carbonaceous material or a macromolecular material. A product including the second material is collected and may be processed further to yield a modified product or a composite.

27 Claims, 7 Drawing Sheets

(56) References Cited

U.S. PATENT DOCUMENTS

| | | | |
|---|---|---|---|
| 7,951,911 | B2 | 5/2011 | Jagota et al. |
| 7,955,585 | B2 | 6/2011 | Afzali-Ardakani et al. |
| 7,964,174 | B2 | 6/2011 | Dubin et al. |
| 7,968,191 | B2 | 6/2011 | Hampden-Smith et al. |
| 2006/0239882 | A1 | 10/2006 | Seo et al. |
| 2008/0264831 | A1 | 10/2008 | Stenger et al. |
| 2009/0081095 | A1 | 3/2009 | Wasas |
| 2011/0008244 | A1 | 1/2011 | Brutchey et al. |

OTHER PUBLICATIONS

Lim et al, Synthetic Metals, 2003, 139, 521-527.*
Meng et al, Progress in Natural Science, 2009, 19, 801-810.*
Yang et al, Nano, 2012, 6(1), 205-211.*
Chen et al, J. Phys. Chem. C, 2010, 114, 19885-890.*
Ji et al, J. Am. Chem. Soc., 2011, 133, 18522-18525.*
Ji, Junyi et al, J. Mater. Chem., 2011, 21, 14498-14501.*
J Cech et al., Functionalization of multi-walled carbon nanotubes: Direct proof of sidewall thiolation, Phys. Stat. Sol. (b) 243, No. 13, 2006, pp. 3221-3225.
C.H. Chang et al., Preparationand Characterizationof Carbon-Sulfursurface Compounds, Carbon vol. 19, 1981, pp. 175-186.
M. Frasconi et al., Protein immobilization at gold-thiol surfaces and potential for biosensing, Anal Bioanal Chem, 2010, 398:1545-1564.
J. Hu et al., Efficient method to functionalize carbon nanotubes with thiol groups and fabricate gold nanocomposites, Chemical Physics Letters 401, 2005, pp. 352-356.
J.K. Lim et al., Selective thiolation of single-walled carbon nanotubes, Synthetic Metals 139, 2003, pp. 521-527.
L. Meng et al., Advanced technology for functionalization of carbon nanotubes, Progress in Natural Science 19, 2009, pp. 801-810.
L. Minati et al., Characterization of thiol-functionalized carbon nanotubes on gold surfaces, Surface Science 604, 2010, pp. 1414-1419.
N.O.V. Plank et al., Thiolation of single-wall carbon nanotubes and their self-assembly, Applied Physics Letters 85, No. 15, Oct. 2004, pp. 3229-3231.
Y-P. Sun et al. Functionalized Carbon Nanotubes: Properties and Applications, Acc. Chem. Res. 35, 2002, pp. 1096-1104.
A.J. Owen et al., The reactions of carbon with sulphur compounds. Part 2.—The reaction of hydrogen sulphide with types of carbon, Trans. Faraday Soc. 49, 1953, pp. 1207-1212.
K.W. Sykes et al., The reactions of carbon with sulphur compounds. Part 4. Adsorption of gaseous sulphur and carbon disulphide by charcoal, Trans. Faraday Soc. 52, 1956, pp. 660-671.
W. Tremel et al., New Synthetic Approaches to Functionalized Chalcogenide Nanostructures, Proceedings of the Twentieth (2010) International Offshore and Polar Engineering Conference Beijing, China, Jun. 20-25, 2010, 8 pages.
Y. Xiao et al., The functionalization of multi-walled carbon nanotubes by in situ deposition of hydroxyapatite, Biomaterials 31, 2010. pp. 5182-5190.
D.S. Kim, International Search Report and written opinion of the international search authority for PCT/US2013/026314, mailed Jun. 26, 2013, 12 pages.

* cited by examiner

MULTIFUNCTIONAL MATERIALS AND COMPOSITES

CROSS-REFERENCE TO RELATED APPLICATIONS

This application is a U.S. National Phase Application of International Patent Application No. PCT/US2013/026314 filed Feb. 15, 2013, which claims the benefit of U.S. Application Ser. No. 61/599,250, filed on Feb. 15, 2012, the contents of both of which are incorporated herein by reference in their entirety.

STATEMENT OF GOVERNMENT INTEREST

This invention was made with government support under DE-SC0001016 awarded by the Department of Energy. The government has certain rights in the invention.

TECHNICAL FIELD

This invention relates to materials having chalcogen-containing functional groups and oxygen-containing functional groups.

BACKGROUND

Because of their wide range of physical and chemical properties, chalcogen-containing functional groups such as thiols are desirable chemical moieties which can provide additional functionalities to carbonaceous materials and polymer materials for diverse industrial applications including composite productions, sensor fabrications and drug delivery. Carbonaceous materials and polymer materials often exhibit oxygen-containing functional groups. Functionalization of those materials by chalcogen-containing groups is typically carried out by crosslinking the oxygen-containing functional groups with chalcogen-containing molecules.

SUMMARY

Covalently bonded materials are materials in which atoms are bonded to each other by covalent or partially covalent bonds. The covalently bonded materials described herein can be carbonaceous materials, macromolecular materials, or combinations or composites thereof. As used herein, "carbonaceous material" generally refers to a high-molecular-weight material derived from organic or biological precursors and having an elevated carbon:hydrogen ratio. In one example, a carbonaceous material has a molar mass of at least 500 g/mol or at least 1000 g/mol and a carbon:hydrogen ratio of at least 0.5. As used herein, a "macromolecular material" generally refers to an organic, biological, or modified biological molecular compounds of high relative molecular mass having repeat units of low relative molecular mass. In one example, a macromolecular material is an organic macromolecular material, a biological macromolecular material, or a modified biological material having a molar mass of at least 500 g/mol or at least 1000 g/mol and including a repeat unit having a molar mass of 200 g/mol or less. In another example, a macromolecular material has at least 5 repeat units, each repeat unit having a molar mass of 200 g/mol or less.

As used herein, "chalcogen" refers to sulfur, selenium and tellurium, and "chalcogenide compound" generally refers to a compound having a chalcogen with a partially negative charge as predicted from an electronegativity scale. One popular electronegativity scale was devised by Pauling. In one example, a chalcogenide compound includes at least one chalcogen selected from the group consisting of sulfur, selenium, and tellurium, and at least one element selected from Groups 1, 2, and 13-16 in the periodic table. Chalcogenide compounds described herein may be a solid at room temperature and atmospheric pressure or a liquid with a boiling point greater than 50° C. at 100 kPa. In some examples, at least one chalcogen in the chalcogenide compound is not bonded to oxygen or hydrogen.

The carbonaceous and macromolecular materials can be nanomaterials. According to the draft definition for public comment by the European Commission (EC) released in 2010 and as used herein, a nanomaterial is a material that consists of particles with one or more external dimensions in the size range 1 nm-100 nm for more than 1% of their number; and/or has internal or surface structures in one or more dimensions in the size range 1 nm-100 nm; and/or has a specific surface area by volume greater than 60 $m^2/cm^3$, excluding materials consisting of particles with a size lower than 1 nm.

Carbonaceous nanomaterials include humic acids, fulvic acids, reduced humic acids, reduced fulvic acids, graphenol, graphene, graphite oxides (or called graphene oxides), reduced graphene oxides, carbon nanotubes (CNTs), carbon nanoparticles, nanodiamonds, graphite nanofibers, graphite nanoplatelets and nanoporous carbons. Macromolecular nanomaterials can be in a form of nanoparticles, nanobeads, nanorods, nanofibers, or the like. Macromolecular nanomaterials can be nanoporous. Carbonaceous nanomaterials and macromolecular nanomaterials have been extensively explored for various applications including electronics, sensing, drug delivery, composite production, and environmental remediation.

The covalently bonded materials can have a plurality of functional groups internally (e.g., extending from a surface of an internal pore) or externally (e.g., extending from an external surface of the material). Some common functional groups contain oxygen atoms that are covalently bonded to hydrogen and/or carbon atoms. Examples of oxygen-containing functional groups include hydroxyl, alkoxide, ether, acetal, carbonyl, carboxylate, nitrate, sulfate, phosphate, and carboxylic acid groups. Other common functional groups contain chalcogen atoms. Some common chalcogen-containing functional groups include chalcogen atoms covalently bonded to hydrogen and/or carbon atoms, but not to oxygen atoms. Examples include thiol, sulfide (or thioether), disulfide, polysulfide, thiolate, thioactal, theoketal, thioketone, thioester, thionoester, dithioester, thiolactone, thiolactone, dithiolactone, dithiocarbamate and dithiolethione.

The oxygen-containing functional groups and the chalcogen-containing functional groups have different chemical, physical, biological, pharmacological, or other properties. For example, the former has a stronger affinity for hard cations, while the latter for soft cations. Furthermore, the chalcogen-containing functional groups tend to become oxidized more easily than the oxygen-containing functional groups.

Multifunctional covalently bonded materials are covalently bonded materials that have different types of functional groups in the same body of the material structure (e.g., a plurality of chalcogen-containing functional groups and a plurality of oxygen-containing functional groups). Such materials can be useful, for example, in sequestering both hard metal cations (e.g., $Al^{3+}$, $Ba^{2+}$, $Be^{2+}$, $Co^{3+}$, $Cr^{3+}$, $Fe^{3+}$, $Mn^{2+}$, $Sr^{2+}$, $U^{4+}$, $UO_2^{2+}$, and $VO^{2+}$) and soft metal cations (e.g., $Ag^+$, $Cd^{2+}$, $Cu^+$, $Hg^{2+}$, $Hg^+$, $CH_3Hg^+$, $Tl^{3+}$, $Tl^+$) as well as borderline metal cations (e.g., $Co^{2+}$, $Cu^{2+}$, $Fe^{2+}$, $Ni^{2+}$, $Pb^{2+}$, $Zn^{2+}$). Such materials can be further functionalized through cross-linking for various applications including electronics, sensing, drug delivery, composites production and environmental remediation.

In a first general aspect, contacting a first material having a molar mass of at least 500 g/mol or 1000 g/mol and having oxygen-containing functional groups with a chalcogenide compound including at least one chalcogen, and initiating a chemical reaction between the first material and the chalcogenide compound, thereby replacing oxygen in some of the oxygen-containing functional groups with chalcogen from the chalcogenide compound to yield a second material having chalcogen-containing functional groups and oxygen-containing functional groups. The chalcogenide compound is a solid or a liquid with a boiling point greater than 50° C. at 100 kPa including (i) at least one chalcogen selected from the group consisting of sulfur, selenium, and tellurium, and (ii) at least one element selected from Groups 1, 2, and 13-16 in the periodic table, with at least one chalcogen in the chalcogenide compound not bonded to oxygen or hydrogen.

Implementations may include one or more of the following features. The oxygen-containing functional groups of the first material may include hydroxyl groups, alkoxide groups, or a combination thereof. In some cases, the oxygen-containing functional groups of the first material are selected from the group consisting of hydroxyl groups and alkoxide groups.

In one implementation, the first material includes or consists of a carbonaceous nanomaterial having a carbon: hydrogen ratio of at least 0.5. In some cases, the carbonaceous nanomaterial is porous. A plurality of hydroxyl or alkoxide groups may extend from an internal or external surface of the porous nanomaterial. In certain implementations, the first material includes or consists of an organic macromolecular material, a biological macromolecular material, or a modified biological macromolecular material including a repeat unit having a molar mass of 200 g/mol or less.

The chalcogenide compound may include boron or phosphorus. Contacting the first material with the chalcogenide compound may include combining the first material and the chalcogenide compound in an inorganic medium or an organic solvent, or forming the chalcogenide compound in situ in the presence of the first material. In some cases, the inorganic medium is a molten salt or an ionic liquid. In some cases, contacting the first material with the chalcogenide compound includes forming a mixture including the first material and the chalcogenide compound. The mixture may be in a container whose atmosphere is not directly in contact with air. Initiating the chemical reaction between the first material and the chalcogenide compound may include subjecting the mixture to a selected temperature and pressure or heating the mixture at a temperature in a range between 300° C. and 700° C. under a reduced pressure, in an inert gas environment, or both.

In some implementations, the second material is separated from by-products formed in the chemical reaction. The second material may have a molar mass of at least 500 g/mol or at least 1000 g/mol. In some cases, a majority of chalcogen atoms in the chalcogen-containing functional groups are not directly bonded to more than one oxygen or more than one fluorine atom.

A second general aspect includes a product formed by the process of the first general aspect. The product may be in the form of a coating, a film, a monolith, a powder, or a dispersion. The product may be electrically conductive, thermally conductive, or both. In some cases, the product is optically transparent or translucent. The product may be porous or nanoporous. In certain cases, a majority of the chalcogen-containing functional groups in the product are thiol groups.

In a third general aspect, a material includes the product of the second general aspect deposited on a surface of the material.

In a fourth general aspect, a composite includes the product of the second general aspect.

A fifth general aspect includes a modified product formed by chemically reducing, oxidizing, metathesizing, hydrolyzing, dehydrating, decomposing, and/or deprotonating the product of the second general aspect.

A sixth general aspect includes a modified product formed by functionalizing the product of the second general aspect with organic, inorganic and/or biological moieties.

In a seventh general aspect, a material including the modified product of the fifth general aspect or the sixth general aspect deposited on a surface of the material.

In an eighth general aspect, a composite includes the modified product of the fifth general aspect or the sixth general aspect.

Thus, particular embodiments have been described. Variations, modifications, and enhancements of the described embodiments and other embodiments can be made based on what is described and illustrated. In addition, one or more features of one or more embodiments may be combined. The details of one or more implementations and various features and aspects are set forth in the accompanying drawings, the description, and the claims below.

DETAILED DESCRIPTION

Figure 1:
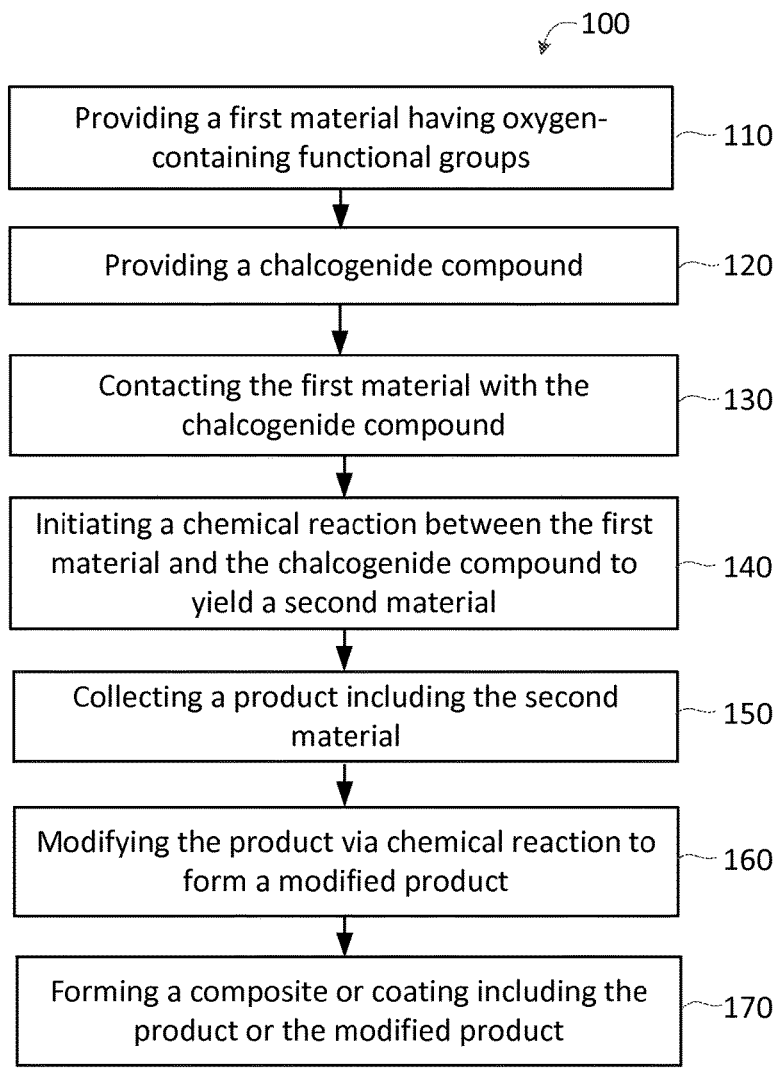
FIG. 1 is a flowchart of an exemplary process for forming a covalently bonded material that has both oxygen-containing functional groups and chalcogen-containing functional groups.

Referring to FIG. 1, process 100 for preparing materials includes providing a first material having a plurality of oxygen-containing functional groups (110), providing at least one chalcogenide compound (120) having at least one chalcogen, and contacting the first material with the chalcogenide compound (130). The first material is a macromolecular material. The first material includes or consists of macromolecular material having a molar mass of at least 500 g/mol or at least 1000 g/mol. Oxygen-containing functional groups in the first material include, for example, hydroxyl, ether, acetal, carbonyl, carboxylate, nitrate, sulfate, phosphate, and carboxylic acid groups. In some implementations, the macromolecular material is a carbonaceous material (e.g., a carbonaceous nanomaterial) having a carbon:hydrogen ratio of at least 0.5. In some cases, the carbonaceous nanomaterial is porous. A plurality of hydroxyl or alkoxide groups may extend from an internal or external surface of the porous nanomaterial. In certain implementations, the macromolecular material includes or consists of an organic macromolecular material, a biological macromolecular material, or a modified biological macromolecular material including a repeat unit having a molar mass of 200 g/mol or less. In some examples, the organic, biological, or modified biological macromolecular has at least five repeat units. The chalcogenide compound is a solid or a liquid with a boiling point greater than 50° C. at 100 kPa including (i) at least one chalcogen selected from the group consisting of sulfur, selenium, and tellurium, and (ii) at least one element selected from Groups 1, 2, and 13-16 in the periodic table. At least one chalcogen in the chalcogenide compound is not bonded to oxygen or hydrogen.

A chemical reaction is initiated between the first material and the chalcogenide compound (140), thereby replacing oxygen in some of the oxygen-containing functional groups with chalcogen in the chalcogenide compound to yield a second material including a plurality of oxygen-containing functional groups and a plurality of chalcogen-containing functional groups. The second material is a macromolecular material having a molar mass of at least 500 g/mol or at least 1000 g/mol. The chalcogen-containing functional groups include, for example, thiol, sulfide (or thioether), disulfide, polysulfide, thiolate, thioactal, theoketal, thioketone, thioester, thionoester, dithioester, thiolactone, thiolactone, dithiolactone, dithiocarbamate, and dithiolethione.

A product including the second material is collected (150). The product may be modified to form a modified product (160). Modification includes, for example, chemically reducing, oxidizing, metathesizing, hydrolyzing, dehydrating, decomposing, and/or deprotonating the product. Modification may result in functionalizing the product with organic, inorganic and/or biological moieties. In some cases, a composite including the product or the modified product is formed (170).

In various implementations, one or more operations shown in FIG. 1 may be omitted, one or more additional operations may be added, or both. In some cases, the order of the operations shown in FIG. 1 may be changed, or selected combinations of the operations may be performed.

First materials with different functional groups have different chemical, physical, biological, pharmacological, or other properties. For example, the oxygen-containing functional groups have a stronger affinity for hard cations, while the chalcogen-containing functional groups have a stronger affinity for soft cations, based on Hard-Soft Acid-Base Theory. For example, the chalcogen-containing functional groups such as thiol can be used as a crosslinking agent to form covalent bonds with enes and ynes. Furthermore, the chalcogen-containing functional groups tend to become oxidized more easily than the oxygen-containing functional groups.

In some cases, the carbonaceous material includes polycyclic aromatic hydrocarbons. Examples of the carbonaceous materials include coal tar pitch, mesogenic pitch, mesophase pitch, and petroleum pitch. The carbonaceous materials may include a mesophase, such as carbonaceous mesophase or bulk mesophase. In some cases, the carbonaceous materials are from biogenic materials. Examples of the carbonaceous materials include soot, dehydrated carbohydrates, biochar, activated carbon, and the like.

In some cases, the carbonaceous material includes carbonaceous nanomaterials. Carbonaceous nanomaterials include, for example, humic acids, fulvic acids, reduced humic acids, reduced fulvic acids, graphenol, graphene oxide, reduced graphene oxide, carbon nanotubes, carbon nanoparticles, nanodiamonds, graphite nanofibers, graphite nanoplatelets and nanoporous carbons, activated carbon, mesoporous carbon, or the like. Examples 1-12 illustrate some implementations of process 100 in which the first material is graphene oxide. Graphene oxides are oxidized graphene sheets which are typically tens of nanometers to several micrometers in lateral dimension. Example 13 illustrates an implementation of process 100 in which the first material is oxidized carbon spheres. Example 14 illustrates an implementation of process 100 in which the first material is nanoporous carbon.

The carbonaceous materials may have oxygen-containing functional groups that are originated from their precursors. The carbonaceous materials may have oxygen-containing functional groups that are formed during their production. The carbonaceous materials may have oxygen-containing functional groups that are introduced in a postsynthetic functionalization process.

In some implementations, the first material is mixed with another material. Example 15 illustrates one implementation of process 100 in which a carbonaceous material is mixed with nano-sized tungsten powder. Example 16 illustrates an implementation of process 100 in which a carbonaceous material is mixed with $TiO_2$ nanoparticles.

In some implementations of process 100, the first material having a plurality of oxygen-containing functional groups includes macromolecules. Examples of macromolecules are polymers and biopolymers. According to IUPAC, biopolymers are macromolecules formed by living organisms. Examples of the polymers include polyols, polyketones, polyethers, polyesters, and polycarbonates. Examples of the biopolymers include polysaccharides such as cellulose, chitin, chitosan, starch, pectins, dextrins, dextrans, gums, and the like. Examples of the biopolymers include non-polysaccharides such as lignin and the like. In some cases, biopolymers are modified biopolymers. Examples of the biopolymers include proteins and nucleic acids. Example 17 illustrates one implementation of process 100 in which the biopolymer is cellulose. Cellulose has the formula $(C_6H_{10}O_5)_n$ and is a polysaccharide consisting of a linear chain of several hundred to over ten thousand β(1→4) linked D-glucose units. The monomeric unit has a molecular mass of 162 g/mol. Examples of modified biopolymers include methyl cellulose, ethyl cellulose, oxidized starch, acetylated starch, cyclodextrins, and the like. Example 18 illustrates one implementation of process 100 in which the modified biopolymer is ethyl cellulose. Other examples of the biopolymers include proteins and nucleic acids.

The macromolecular materials may have oxygen-containing functional groups that are originated from their precursors. The macromolecular materials may have oxygen-containing functional groups that are formed during production. The macromolecular materials may have oxygen-containing functional groups that are introduced in a postsynthetic functionalization process. In some cases, the macromolecular materials are formed with C—O—C or O—C—O linkages in their repeating units. In some cases, macromolecular materials contain a plurality of hydroxyl groups.

In some examples, the chalcogenide compound is a binary compound that includes at least one chalcogen element and at least one element in Groups 13 to 16 in the periodic table. In some cases, the at least one Group 13-16 element is not carbon. In some cases, the chalcogenide compound includes a boron chalcogenide ($B_xX_y$: B=boron; X=S, Se, and Te). In some cases, the chalcogenide compound includes $B_2S_3$ or $BS_2$. In some cases, the chalcogenide compound includes a phosphorous chalcogenide ($P_xX_y$: P=phosphorous; X=S, Se, and Te). In some cases, the chalcogenide compound includes $P_2S_5$ (or $P_4S_{10}$). Examples 1 and 12 illustrate some implementations of process 100 in which the chalcogenide compound is $P_2S_5$.

In some cases, the chalcogenide compound is a multinary compound. One example of multinary chalcogenide compounds is sulfurated borohydrides (e.g., $NaBH_2S_3$), or a selenium or tellurium analog (e.g, $NaBH_2Se_3$ or $NaBH_2Te_3$, respectively). Another example of multinary chalcogenide compounds is salts containing thiocyanate ($SCN^-$) ion, such as KSCN, or organothiocyanates, such as phenyl thiocyanate. Another example of multinary chalcogenide compounds is thiourea, thiocarbamates and dithiocarbamates. In some cases, the chalcogenide compound is a complex between a chalcogenide compound and some molecules, such as $P_4S_{10}$-pyridine complex.

In some cases, providing a chalcogenide compound includes forming the compound in situ by reacting at least one chalcogen element with at least one solid element chosen from the Groups 1, 2, 13, 14, 15 and 16. As used herein, in situ formation of the chalcogenide compound includes formation in the presence of the first material. For example, the reaction of sulfur with boron may yield boron sulfides. In some cases, providing a chalcogenide compound includes forming the compound in situ by reacting at least one chalcogen element with a compound.

In some cases, providing a chalcogenide compound includes forming the compound in situ by reacting at least one chalcogen-containing compound with a compound or an element. In some cases, the chalcogenide compound is an adduct or a complex between a chalcogen-containing compound and a molecular compound. For example, $P_2S_5$ react with pyridine to form a complex, $P_4S_{10}$-pyridine, in situ.

In process 100, providing a chalcogenide compound may include forming the compound in situ by reacting at least one chalcogen element with at least one solid element chosen from the Groups 1, 2, 13, 14, 15 and 16. Examples 2-10 and 13-16 illustrate some implementations of process 100 in which boron sulfide, phosphorous sulfide, and boron selenide compounds were prepared in situ by reacting sulfur or selenium with amorphous boron powder or phosphorous powder. In some cases, providing a chalcogenide compound includes forming the compound in situ by reacting at least one chalcogen element with at least one solid element chosen from the Groups 1 and 2. In some cases, providing a chalcogenide compound includes forming the compound in situ by reacting at least one chalcogen element with at least one inorganic compound.

In some cases, providing a chalcogenide compound includes forming the compound in situ as a precipitate or dissolved form in an organic solvent. Example 11 illustrates one implementation of process 100 in which a sulfurated borohydride was prepared in situ from sulfur and $NaBH_4$ in a solvent-refluxing condition.

In some implementations of process 100, providing a chalcogenide compound includes mixing a first material having a plurality of oxygen-containing functional groups with an inorganic compound. In some cases, providing a chalcogenide compound includes dispersing or mixing the compound in an inorganic medium. In some cases, providing a chalcogenide compound includes dissolving the compound in an inorganic medium. Examples 4-7 illustrate some implementations of process 100 in which sodium chloride (NaCl) was chosen as the inorganic medium in which graphene oxide, boron powder and sulfur powder were mixed together homogeneously. In some cases, the inorganic medium is a molten salt or an ionic liquid.

In some implementations, providing a chalcogenide compound includes dissolving the compound in an organic solvent. In some cases, providing a chalcogenide compound includes dispersing the compound in an organic solvent. In some cases, providing a chalcogenide compound includes mixing a first material having a plurality of oxygen-containing functional groups together in an organic solvent. Examples 11, 12, 17 and 18 illustrate some implementations of process 100 in which graphene oxide and chalcogenide compounds were mixed together in organic solvents such as 2-methyltetrahydrofuran (2-MeTHF) and acetonitrile.

In process 100, contacting a first material having oxygen-containing functional groups with a chalcogenide compound includes heating the material and the compound in an oxygen- and/or moisture-limited environment. An oxygen- and/or moisture-limited environment is defined as an environment in which the amount of oxygen or moisture is controlled to be lower than the amount found in an uncontrolled environment. In some cases, heating is carried out at temperatures from about 300° C. to about 700° C. In some cases, heating is carried out under reduced pressure (e.g., a pressure less than atmospheric pressure). Examples 1-10 and 13-16 illustrate some implementations of process 100 in which a carbonaceous material or its mixture with another material was sealed in an evacuated silica ampule together with chalcogen sources, and then heated in a furnace at 500-600° C.

In some implementations, heating is carried out under a refluxing condition. In some cases, heating is carried out at temperatures from about 50° C. to about 300° C. Examples 17 and 18 illustrate some implementations of process 100 in which a polymeric material was reacted together with $P_2S_5$ in acetonitrile (boiling point=81-82° C.) under a solvent-refluxing condition. In some cases, heating is carried out under a solvothermal condition. A solvothermal condition is a condition in which a solvent liquid is under a pressure higher than 1 bar. Examples 21 and 26 illustrate some implementations of process 100 in which graphene oxide was reacted together with $P_2S_5$ in pyridine (boiling point=115° C.) in a closed container at 120 or 150° C. Examples 27 and 28 illustrate some implementations of process 100 in which multi-walled carbon nanotubes were reacted together with $P_2S_5$ in pyridine in a closed container at 120 or 160° C. Examples 29 and 30 illustrate some implementations of process 100 in which cellulose was reacted together with $P_2S_5$ in pyridine in a closed container at 100° C.

In some implementations of process 100, collecting a product including the second material includes removing a by-product containing oxygen atoms. In some cases, collecting the product includes treating the second material to chemically reduce polychalcogenide functional groups. Examples 2-11, 13, 14, 17, and 18 illustrate some implementations of process 100 in which a sodium borohydride (NaBH$_4$) solution was used to reduce the second material.

In some implementations, the first material can be in a coating deposited on a substrate. Example 19 illustrates one implementation in which graphene oxide coating deposited on a glass slide was used as the material that reacted with a chalcogenide compound.

Optionally modifying the product (160) includes treating the product to yield another material. The treatment may modify or functionalize the product with organic, inorganic and/or biological moieties. Example 20 illustrates one implementation in which the product of Example 2, graphene oxide having both oxygen-containing functional groups and sulfur-containing functional groups, was functionalized with silver nanoparticles. The majority of the oxygen-containing functional groups were hydroxyl groups, based on the XPS results. The silver triflate precursor was dissolved in DMF together with the product of Example 2. It is believed that silver nanoparticles were likely due to the reduction of silver ions by hydroxyl groups coexistent in the product. Example 31 illustrates one implementation in which the product of Example 28, multi-walled carbon nanotubes having both oxygen-containing functional groups and sulfur-containing functional groups, were functionalized with gold nanoparticles, by mixing a dispersion of the product of Example 28 with a dispersion of gold nanoparticles.

Forming a composite (170) includes treating the product to produce a composite. In some cases, composites include polymer composites. In some cases, composites include deposits or films on substrates. Example 32 illustrates one implementation in which the product of Example 22, graphene sheets having both oxygen-containing functional groups and sulfur-containing functional groups, were deposited on a gold thin film.

In some implementations, the produced materials are electrically and/or thermally conducting. In some implementations, the produced materials are optically transparent or translucent. In some implementations, the produced materials are porous.

The materials and composites described herein can be used in a variety of ways including, but not limited to, adsorbents, absorbents, nanocomposites, catalysts, catalyst supports, oxidizing agents, reducing agents, ion exchange materials, separation materials, magnetic separation materials, electrodes, sensors, electrical materials, electronic materials, coating materials, thin film materials, electrical inks, conductive inks, transparent conductive inks, magnetic materials, electromagnetic wave absorbers, microwave absorbers, microwave-assisted heating materials, bio-implants, structure reinforcing materials, construction materials, solar energy collectors, supercapacitors, pseudocapacitors, fire retardants, paint thickeners, additives, adhesives, ink jet coatings, fillers, ionic conductors, cross-liking agents, bioconjugation agents, bioreactors, enzyme catalysts, enzyme supports, active battery components, toxin removal materials, chemical removal materials, waste removal materials, hazard removal materials, chemical decontaminants, bioactive decontaminants, odor elimination materials, arsenic removal materials, heavy metal removal materials, metal scavenging materials, precious metal scavenging materials, drug delivery materials, water purification materials, water desalination materials, capacitive deionization electrodes, vapor sorption materials, gas sorption materials, oil sorption materials, oil extraction materials, and the like.

The following examples are provided for illustration. It should be appreciated by those of skill in the art that the techniques disclosed in the following examples are considered to be exemplary. However, those of skill in the art should, in light of the present disclosure, appreciate that many changes can be made in the specific embodiments that are disclosed without departing from the spirit and scope of this disclosure.

EXAMPLES

Example 1

About 0.2 g of graphene oxide (GO) dispersed in deionized water (0.1 wt %, pH~1) was mixed with 130 mL of 1M NaOH aqueous solution. The solution was centrifuged and the supernatant was decanted. 100 mL of deionized water was added to the precipitate. The precipitate in deionized water was sonicated until it became homogeneous by visual inspection. The solution was dried in a lab oven at 110° C. overnight. 0.7422 g of P$_2$S$_5$ powder was mixed with the dried precipitate and the mixture was subsequently placed in a silica tube (11 mm I.D.). After the silica tube was evacuated and flamed-sealed, the mixture in the silica ampule was gradually heated at 100° C./hr to 500° C., kept for 10 hrs, and radiatively cooled to room temperature. After the reaction, the silica ampule was intact, and there was no visible indication of corrosion on the inner surface. Once the product was taken out after breaking the silica ampule, it was ground and repeatedly washed with degassed hot water (~80° C.) until the supernatant became colorless. The precipitate was dried to give a final product. The C:O:S ratio of the product was 13.2:1:1.98 from the X-ray photoelectron spectroscopy (XPS) results.

Example 2

Figure 2:
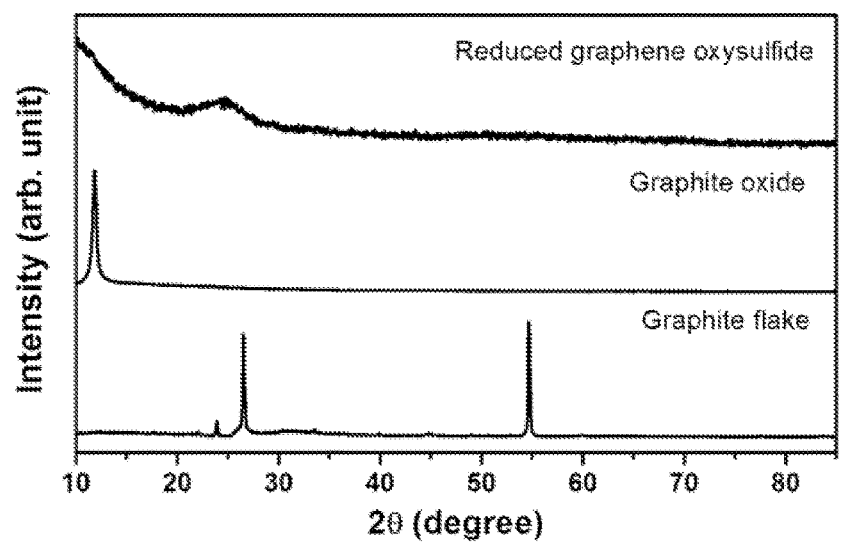
FIG. 2 shows the powder X-ray diffraction of the final product of Example 2 compared to that of graphene oxide (GO) and graphite flakes.
Figure 3:
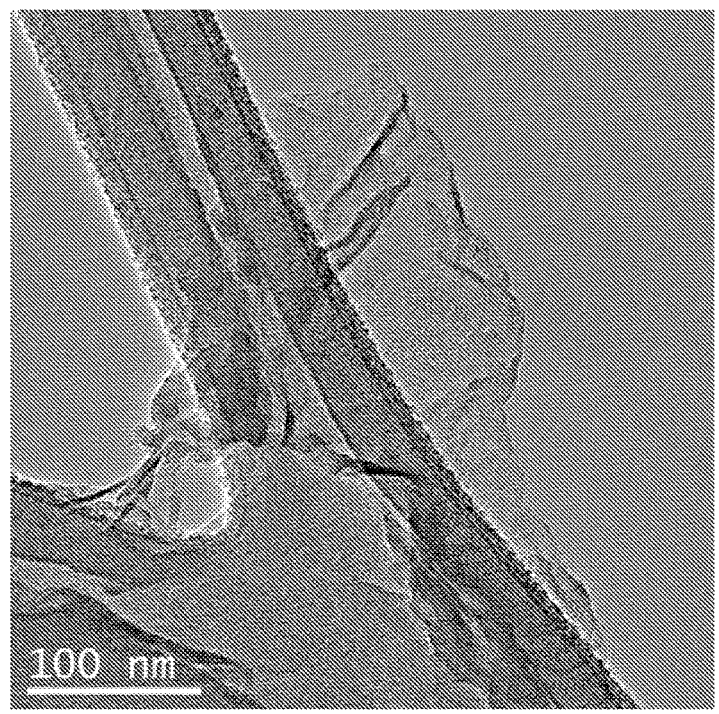
FIG. 3 shows a transmission electron microscopy (TEM) image of the final product of Example 2.

About 0.2 g of graphene oxide (GO) dispersed in deionized water (0.1 wt %, pH~1) was mixed with 130 mL of 1M NaOH aqueous solution. The solution was centrifuged and the supernatant was decanted. 0.0360 g of amorphous boron powder and 100 mL of deionized water were added to the precipitate. The mixture was sonicated until it became homogeneous by visual inspection. The mixture solution was dried in a lab oven at 110° C. overnight. 0.2138 g of sulfur powder was mixed with the dried precipitate and the mixture was subsequently placed in a silica tube (11 mm I.D.). After the silica tube was evacuated and flamed-sealed, the mixture in the silica ampule was gradually heated at 100° C./hr to 500° C., kept for 10 hrs, and radiatively cooled to room temperature. After the reaction, the silica ampule was intact, and there was no visible indication of corrosion on the inner surface. Once the product was taken out after breaking the silica ampule, it was ground and sonicated in carbon disulfide. After centrifugation and decantation, the precipitate was dried in air. The product was then repeatedly washed with degassed hot water (~80° C.) until the supernatant became colorless. 2 mL of 12 wt % sodium borohydride (NaBH$_4$) solution in aqueous 14M NaOH was added to the product and then the mixture solution was sonicated for 10 min. A sufficient volume of 1M HCl solution was added to the solution to give a final pH of about 1. The solution was centrifuged and decanted. The precipitate was rinsed multiple times with deionized water and dried to give a final product. FIG. 2 shows the powder X-ray diffraction of the final product compared to that of GO and graphite flakes. The C:O:S ratio of the product was 19.3:1:2.14 from the X-ray photoelectron spectroscopy (XPS) results. FIG. 3 shows a transmission electron microscopy (TEM) image of the final product.

Example 3

Figure 4:
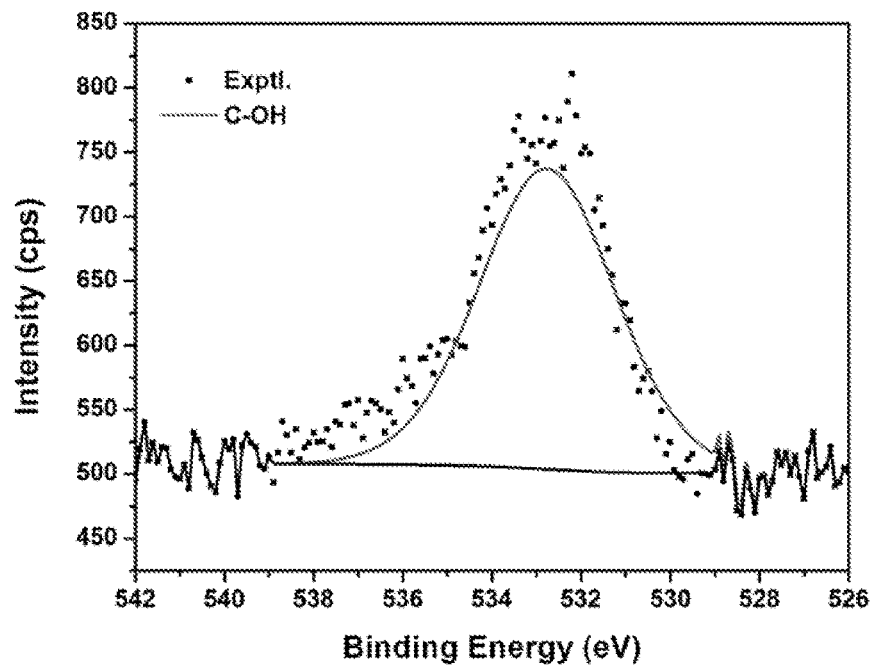
FIG. 4 and FIG. 5 are X-ray photoelectron spectra (XPS) of O(1s) and S(2p) core level regions for the final product of Example 3, respectively.
Figure 5:
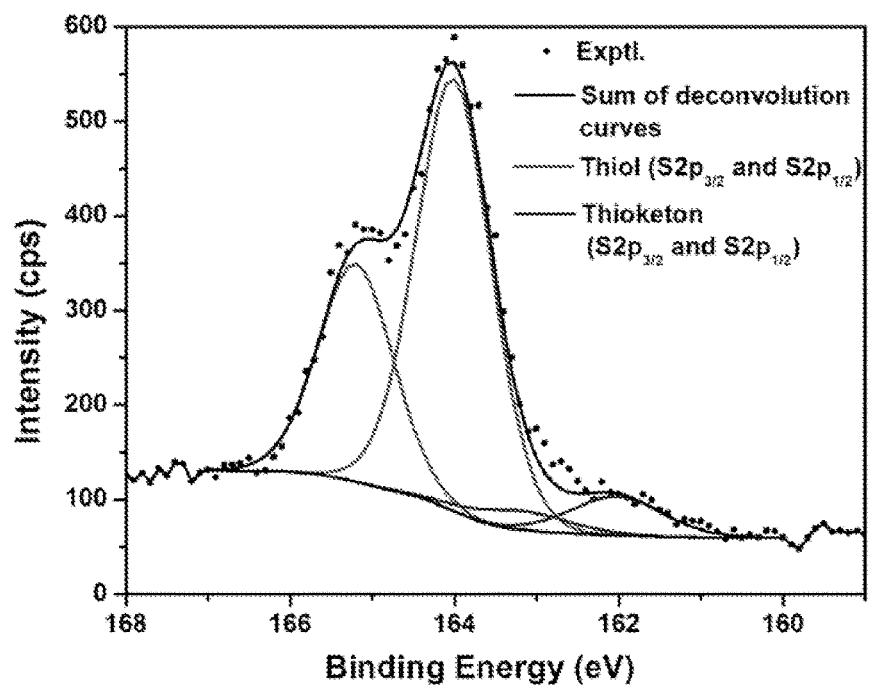

About 0.2 g of graphene oxide (GO) dispersed in deionized water (0.1 wt %, pH~1) was mixed with 130 mL of 1M NaOH aqueous solution. The solution was centrifuged and the supernatant was decanted. 0.0901 g of amorphous boron powder and 100 mL of deionized water were added to the precipitate. The mixture was sonicated until it became homogeneous by visual inspection. The mixture solution was dried in a lab oven at 110° C. overnight. 0.5345 g of sulfur powder was mixed with the dried precipitate and the mixture was subsequently placed in a silica tube (11 mm I.D.). After the silica tube was evacuated and flamed-sealed, the mixture in the silica ampule was gradually heated at 100° C./hr to 500° C., kept for 10 hrs, and radiatively cooled to room temperature. After the reaction, the silica ampule was intact, and there was no visible indication of corrosion on the inner surface. Once the product was taken out after breaking the silica ampule, it was ground and sonicated in carbon disulfide. After centrifugation and decantation, the precipitate was dried in air. The product was then repeatedly washed with degassed hot water (~80° C.) until the supernatant became colorless. 2 mL of 12 wt % sodium borohydride ($NaBH_4$) solution in aqueous 14M NaOH was added to the product and then the mixture solution was sonicated for 10 min. A sufficient volume of 1M HCl solution was added to the solution to give a final pH of about 1. The solution was centrifuged and decanted. The precipitate was rinsed multiple times with deionized water and dried to give a final product. FIG. 4 and FIG. 5 are X-ray photoelectron spectra (XPS) of O(1s) and S(2p) core level regions for the final product, respectively. The C:O:S ratio of the product was 16.8:1:2.18 from the XPS results.

Example 4

About 0.2 g of graphene oxide (GO) dispersed in deionized water (0.1 wt %, pH~1) was mixed with 130 mL of 1M NaOH aqueous solution. The solution was centrifuged and the supernatant was decanted. 0.0360 g of amorphous boron powder, about 2 g of NaCl powder, and 100 mL of deionized water were added to the precipitate. The mixture was sonicated until it became homogeneous by visual inspection. The mixture solution was dried in a lab oven at 110° C. overnight. 0.2138 g of sulfur powder was mixed with the dried precipitate and the mixture was subsequently placed in a silica tube (11 mm I.D.). After the silica tube was evacuated and flamed-sealed, the mixture in the silica ampule was gradually heated at 100° C./hr to 500° C., kept for 10 hrs, and radiatively cooled to room temperature. After the reaction, the silica ampule was intact, and there was no visible indication of corrosion on the inner surface. Once the product was taken out after breaking the silica ampule, it was ground and sonicated in carbon disulfide. After centrifugation and decantation, the precipitate was dried in air. The product was then repeatedly washed with degassed hot water (~80° C.) until the supernatant became colorless. 2 mL of 12 wt % sodium borohydride ($NaBH_4$) solution in aqueous 14M NaOH was added to the product and then the mixture solution was sonicated for 10 min. A sufficient volume of 1M HCl solution was added to the solution to give a final pH of about 1. The solution was centrifuged and decanted. The precipitate was rinsed multiple times with deionized water and dried to give a final product. The C:O:S ratio of the product was 11.6:1:1.54 from the X-ray photoelectron spectroscopy (XPS) results.

Example 5

About 0.2 g of graphene oxide (GO) dispersed in deionized water (0.1 wt %, pH~1) was mixed with 130 mL of 1M NaOH aqueous solution. The solution was centrifuged and the supernatant was decanted. 0.0901 g of amorphous boron powder, about 2 g of NaCl powder, and 100 mL of deionized water were added to the precipitate. The mixture was sonicated until it became homogeneous by visual inspection. The mixture solution was dried in a lab oven at 110° C. overnight. 0.5345 g of sulfur powder was mixed with the dried precipitate and the mixture was subsequently placed in a silica tube (11 mm I.D.). After the silica tube was evacuated and flamed-sealed, the mixture in the silica ampule was gradually heated at 100° C./hr to 500° C., kept for 10 hrs, and radiatively cooled to room temperature. After the reaction, the silica ampule was intact, and there was no visible indication of corrosion on the inner surface. Once the product was taken out after breaking the silica ampule, it was ground and sonicated in carbon disulfide. After centrifugation and decantation, the precipitate was dried in air. The product was then repeatedly washed with degassed hot water (~80° C.) until the supernatant became colorless. 2 mL of 12 wt % sodium borohydride ($NaBH_4$) solution in aqueous 14M NaOH was added to the product and then the mixture solution was sonicated for 10 min. A sufficient volume of 1M HCl solution was added to the solution to give a final pH of about 1. The solution was centrifuged and decanted. The precipitate was rinsed multiple times with deionized water and dried to give a final product. The C:O:S ratio of the product was 16.5:1:3.41 from the X-ray photoelectron spectroscopy (XPS) results.

Example 6

About 0.2 g of graphene oxide (GO) dispersed in deionized water (0.1 wt %, pH~1) was mixed with 130 mL of 1M NaOH aqueous solution. The solution was centrifuged and the supernatant was decanted. 0.0360 g of amorphous boron powder, about 2 g of NaCl powder, and 100 mL of deionized water were added to the precipitate. The mixture was sonicated until it became homogeneous by visual inspection. The mixture solution was dried in a lab oven at 110° C. overnight. 0.2138 g of sulfur powder was mixed with the dried precipitate and the mixture was subsequently placed in a silica tube (11 mm I.D.). After the silica tube was evacuated and flamed-sealed, the mixture in the silica ampule was gradually heated at 250° C./hr to 500° C., kept for 10 hrs, and radiatively cooled to room temperature. After the reaction, the silica ampule was intact, and there was no visible indication of corrosion on the inner surface. Once the product was taken out after breaking the silica ampule, it was ground and sonicated in carbon disulfide. After centrifugation and decantation, the precipitate was dried in air. The product was then repeatedly washed with degassed hot water (~80° C.) until the supernatant became colorless. 2 mL of 12 wt % sodium borohydride ($NaBH_4$) solution in aqueous 14M NaOH was added to the product and then the mixture solution was sonicated for 10 min. A sufficient volume of 1M HCl solution was added to the solution to give a final pH of about 1. The solution was centrifuged and decanted. The precipitate was rinsed multiple times with deionized water and dried to give a final product. The C:O:S ratio of the product was 11.7:1:1.58 from the X-ray photoelectron spectroscopy (XPS) results.

Example 7

About 0.2 g of graphene oxide (GO) dispersed in deionized water (0.1 wt %, pH~1) was mixed with 130 mL of 1M NaOH aqueous solution. The solution was centrifuged and the supernatant was decanted. 0.0901 g of amorphous boron powder, about 2 g of NaCl powder, and 100 mL of deionized water were added to the precipitate. The mixture was sonicated until it became homogeneous by visual inspection. The mixture solution was dried in a lab oven at 110° C. overnight. 0.5345 g of sulfur powder was mixed with the dried precipitate and the mixture was subsequently placed in a silica tube (11 mm I.D.). After the silica tube was evacuated and flamed-sealed, the mixture in the silica ampule was gradually heated at 250° C./hr to 500° C., kept for 10 hrs, and radiatively cooled to room temperature. After the reaction, the silica ampule was intact, and there was no visible indication of corrosion on the inner surface. Once the product was taken out after breaking the silica ampule, it was ground and sonicated in carbon disulfide. After centrifugation and decantation, the precipitate was dried in air. The product was then repeatedly washed with degassed hot water (~80° C.) until the supernatant became colorless. 2 mL of 12 wt % sodium borohydride ($NaBH_4$) solution in aqueous 14M NaOH was added to the product and then the mixture solution was sonicated for 10 min. A sufficient volume of 1M HCl solution was added to the solution to give a final pH of about 1. The solution was centrifuged and decanted. The precipitate was rinsed multiple times with deionized water and dried to give a final product. The C:O:S ratio of the product was 20.5:1:4.33 from the X-ray photoelectron spectroscopy (XPS) results.

Example 8

About 0.2 g of graphene oxide (GO) dispersed in deionized water (0.1 wt %, pH~1) was mixed with 130 mL of 1M NaOH aqueous solution. The solution was centrifuged and the supernatant was decanted. 100 mL of deionized water was added to the precipitate. The precipitate in deionized water was sonicated until it became homogeneous by visual inspection. The solution was dried in a lab oven at 110° C. overnight. 0.1035 g of phosphorous powder and 0.2675 g of sulfur powder were mixed with the dried precipitate and the mixture was subsequently placed in a silica tube (11 mm I.D.). After the silica tube was evacuated and flamed-sealed, the mixture in the silica ampule was gradually heated at 100° C./hr to 500° C., kept for 10 hrs, and radiatively cooled to room temperature. After the reaction, the silica ampule was intact, and there was no visible indication of corrosion on the inner surface. Once the product was taken out after breaking the silica ampule, it was ground and repeatedly washed with degassed hot water (~80° C.) until the supernatant became colorless. 2 mL of 12 wt % sodium borohydride ($NaBH_4$) solution in aqueous 14M NaOH was added to the product and then the mixture solution was sonicated for 10 min. A sufficient volume of 1M of HCl was added to the solution to give a final pH of about 1. The solution was centrifuged and decanted. The precipitate was rinsed multiple times with deionized water and dried to give a final product. The C:O:S ratio of the product was 14.6:1:1.56 from the X-ray photoelectron spectroscopy (XPS) results.

Example 9

About 0.2 g of graphene oxide (GO) dispersed in deionized water (0.1 wt %, pH~1) was mixed with 130 mL of 1M NaOH aqueous solution. The solution was centrifuged and the supernatant was decanted. 0.0360 g of amorphous boron powder and 100 mL of deionized water were added to the precipitate. The mixture was sonicated until it became homogeneous by visual inspection. The mixture solution was dried in a lab oven at 110° C. overnight. 0.5263 g of selenium powder was mixed with the dried precipitate and the mixture was subsequently placed in a silica tube (11 mm I.D.). After the silica tube was evacuated and flamed-sealed, the mixture in the silica ampule was gradually heated at 100° C./hr to 600° C., kept for 10 hrs, and radiatively cooled to room temperature. After the reaction, the silica ampule was intact, and there was no visible indication of corrosion on the inner surface. Once the product was taken out after breaking the silica ampule, it was ground and sonicated in carbon disulfide. After centrifugation and decantation, the precipitate was dried in air. The product was then repeatedly washed with degassed hot water (~80° C.) until the supernatant became colorless. 2 mL of 12 wt % sodium borohydride ($NaBH_4$) solution in aqueous 14M NaOH was added to the product and then the mixture solution was sonicated for 10 min. A sufficient volume of 1M HCl solution was added to the solution to give a final pH of about 1. The solution was centrifuged and decanted. The precipitate was rinsed multiple times with deionized water and dried to give a final product. The C:O:Se ratio of the product was 3.87:1:0.09 from the X-ray photoelectron spectroscopy (XPS) results.

Example 10

About 0.2 g of graphene oxide (GO) dispersed in deionized water (0.1 wt %, pH~1) was mixed with 130 mL of 1M NaOH aqueous solution. The solution was centrifuged and the supernatant was decanted. 0.0901 g of amorphous boron powder and 100 mL of deionized water were added to the precipitate. The mixture was sonicated until it became homogeneous by visual inspection. The mixture solution was dried in a lab oven at 110° C. overnight. 1.3160 g of selenium powder was mixed with the dried precipitate and the mixture was subsequently placed in a silica tube (11 mm I.D.). After the silica tube was evacuated and flamed-sealed, the mixture in the silica ampule was gradually heated at 100° C./hr to 600° C., kept for 10 hrs, and radiatively cooled to room temperature. After the reaction, the silica ampule was intact, and there was no visible indication of corrosion on the inner surface. Once the product was taken out after breaking the silica ampule, it was ground and sonicated in carbon disulfide. After centrifugation and decantation, the precipitate was dried in air. The product was then repeatedly washed with degassed hot water (~80° C.) until the supernatant became colorless. 2 mL of 12 wt % sodium borohydride ($NaBH_4$) solution in aqueous 14M NaOH was added to the product and then the mixture solution was sonicated for 10 min. A sufficient volume of 1M HCl solution was added to the solution to give a final pH of about 1. The solution was centrifuged and decanted. The precipitate was rinsed multiple times with deionized water and dried to give a final product. The C:O:Se ratio of the product was 6.37:1:0.62 from the X-ray photoelectron spectroscopy (XPS) results.

Example 11

About 0.2 g of graphene oxide (GO) dispersed in deionized water (0.1 wt %, pH~1) was mixed with 130 mL of 1M NaOH aqueous solution. The solution was centrifuged and the supernatant was decanted. 100 mL of deionized water was added to the precipitate. The precipitate dispersed in deionized water was sonicated until it became homogeneous by visual inspection. The solution was dried in a lab oven at 110° C. overnight. The precipitate was ground and added to 20 mL of 2-methyltetrahydrofuran (2-MeTHF) and subsequently sonicated for 5 min to use further reaction. 0.4002 g of sulfur powder and 0.1700 g of sodium borohydride ($NaBH_4$) powder were placed in three-neck round bottomed-flask containing 40 mL of 2-MeTHF in water bath. The three-neck round bottomed-flask was heated around 100° C. with stirring and flowing nitrogen gas for 2 hrs. The GO dispersed in 2-MeTHF was added to the three-neck round-bottomed-flask quickly and the water bath was subsequently removed. The solvent-refluxing reaction was carried out at 100° C. for 5 hrs with stirring and flowing nitrogen gas. After the reaction, the solution was centrifuged and the supernatant solution was decanted. The precipitate repeatedly washed with degassed hot water (~80° C.) until the supernatant became colorless. The precipitate was dried to give a final product. The C:O:S ratio of the product was 7.55:1:0.11 from X-ray photoelectron spectroscopy (XPS) results.

Example 12

About 0.2 g of graphene oxide (GO) dispersed in deionized water (0.1 wt %, pH~1) was mixed with 130 mL of 1M NaOH aqueous solution. The solution was centrifuged and the supernatant was decanted. 100 mL of deionized water was added to the precipitate. The precipitate dispersed in deionized water was sonicated until it became homogeneous by visual inspection. The solution was dried in a lab oven at 110° C. overnight. The precipitate was ground and added into a round-bottomed flask containing 40 mL of acetonitrile and 0.7406 g of $P_2S_5$ powder was subsequently added to the round-bottomed flask. The solvent-refluxing reaction was carried out at 130° C. overnight with stirring and flowing nitrogen gas. After the reaction, the solution was centrifuged and the supernatant solution was decanted. The precipitate repeatedly washed with degassed hot water (~80° C.) until the supernatant became colorless. The precipitate was dried to give a final product. The C:O:S ratio of the product was 0.82:1:0.026 from X-ray photoelectron spectroscopy (XPS) results.

Example 13

0.200 g of oxidized carbon spheres was mixed with 0.0901 g of amorphous boron powder and 0.5345 g of sulfur powder and then the mixture was subsequently placed in a silica tube (11 mm I.D.). After the silica tube was evacuated and flamed-sealed, the mixture in the silica ampule was gradually heated at 100° C./hr to 500° C., kept for 10 hrs, and radiatively cooled to room temperature. After the reaction, the silica ampule was intact, and there was no visible indication of corrosion on the inner surface. Once the product was taken out after breaking the silica ampule, it was ground and sonicated in carbon disulfide. After centrifugation and decantation, the precipitate was dried in air. The product was then repeatedly washed with degassed hot water (~80° C.) until the supernatant became colorless. 2 mL of 12 wt % sodium borohydride ($NaBH_4$) solution in aqueous 14M NaOH was added to the product and then the mixture solution was sonicated for 10 min. A sufficient volume of 1M HCl solution was added to the solution to give a final pH of about 1. The solution was centrifuged and decanted. The precipitate was rinsed multiple times with deionized water and dried to give a final product. The C:O:S ratio of the product was 2.51:1:1.72 from the X-ray photoelectron spectroscopy (XPS) results.

Example 14

0.200 g of nanoporous carbon was mixed with 0.0901 g of amorphous boron powder and 0.5345 g of sulfur powder and then the mixture was subsequently placed in a silica tube (11 mm I.D.). After the silica tube was evacuated and flamed-sealed, the mixture in the silica ampule was gradually heated at 100° C./hr to 500° C., kept for 10 hrs, and radiatively cooled to room temperature. After the reaction, the silica ampule was intact, and there was no visible indication of corrosion on the inner surface. Once the product was taken out after breaking the silica ampule, it was ground and sonicated in carbon disulfide. After centrifugation and decantation, the precipitate was dried in air. The product was then repeatedly washed with degassed hot water (~80° C.) until the supernatant became colorless. 2 mL of 12 wt % sodium borohydride ($NaBH_4$) solution in aqueous 14M NaOH was added to the product and then the mixture solution was sonicated for 10 min. A sufficient volume of 1M HCl solution was added to the solution to give a final pH of about 1. The solution was centrifuged and decanted. The precipitate was rinsed multiple times with deionized water and dried to give a final product. The C:O:S ratio of the product was 9.17:1:1.11 from X-ray photoelectron spectroscopy (XPS) results.

Example 15

Figure 6:
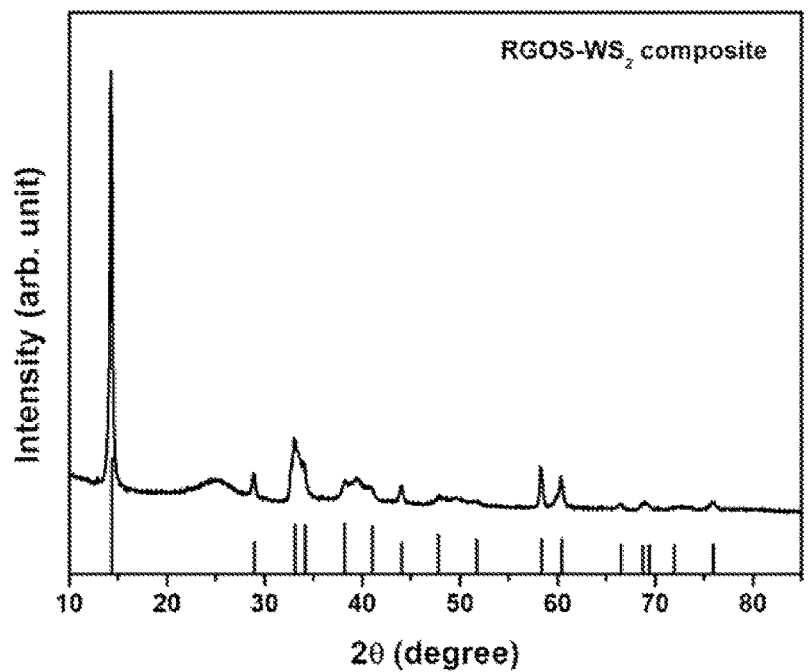
FIG. 6 shows the powder X-ray diffraction pattern of the final product of Example 15 together with the simulated pattern of $WS_2$.

About 0.2 g of graphene oxide (GO) dispersed in deionized water (0.1 wt %, pH~1) was mixed with 130 mL of 1M NaOH aqueous solution. The solution was centrifuged and the supernatant was decanted. 0.0967 g of amorphous boron powder, 0.1063 g of nano-sized tungsten powder, and 100 mL of deionized water were added to the precipitate. The mixture was sonicated until it became homogeneous by visual inspection. The mixture solution was dried in a lab oven at 110° C. overnight. 0.6070 g of sulfur powder was mixed with the dried precipitate and the mixture was subsequently placed in a silica tube (11 mm I.D.). After the silica tube was evacuated and flamed-sealed, the mixture in the silica ampule was gradually heated at 100° C./hr to 500° C., kept for 10 hrs, and radiatively cooled to room temperature. After the reaction, the silica ampule was intact, and there was no visible indication of corrosion on the inner surface. Once the product was taken out after breaking the silica ampule, it was ground and repeatedly washed with degassed hot water (~80° C.) until the supernatant became colorless. The precipitate was dried to give a final product. FIG. 6 shows the powder X-ray diffraction pattern of the final product together with the simulated pattern of $WS_2$.

Example 16

Figure 7:
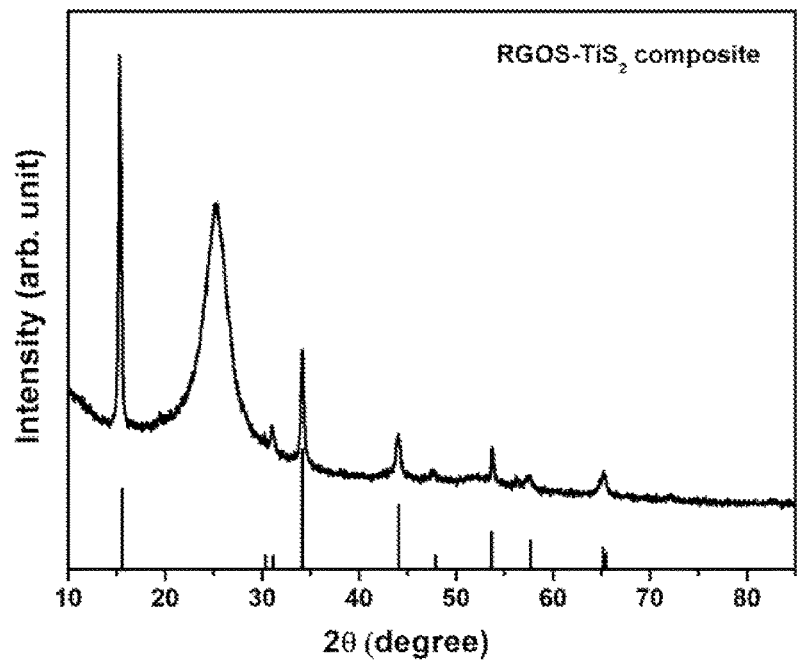
FIG. 7 shows the powder X-ray diffraction pattern of the final product of Example 16 together with the simulated pattern of $TiS_2$.

About 0.2 g of graphene oxide (GO) dispersed in deionized water (0.1 wt %, pH~1) was mixed with 130 mL of 1M NaOH aqueous solution. The solution was centrifuged and the supernatant was decanted. 0.0455 g of amorphous boron powder, 0.1013 g of nano-sized anatase-$TiO_2$ powder, and 100 mL of deionized water were added to the precipitate. The mixture was sonicated until it became homogeneous by visual inspection. The mixture solution was dried in a lab oven at 110° C. overnight. 0.2415 g of sulfur powder was mixed with the dried precipitate and the mixture was subsequently placed in a silica tube (11 mm I.D.). After the silica tube was evacuated and flamed-sealed, the mixture in the silica ampule was gradually heated at 100° C./hr to 600° C., kept for 10 hrs, and radiatively cooled to room temperature. After the reaction, the silica ampule was intact, and there was no visible indication of corrosion on the inner surface. Once the product was taken out after breaking the silica ampule, it was ground and repeatedly washed with degassed hot water (~80° C.) until the supernatant became colorless. The precipitate was dried to give a final product. FIG. 7 shows the powder X-ray diffraction pattern of the final product together with the simulated pattern of $TiS_2$.

Example 17

0.200 g of cellulose filter paper (Whatman, Grade 41, max. ash content=0.007%) was torn into about 1"-sized pieces. The paper pieces and 0.3289 g of $P_2S_5$ powder were added to a round bottomed-flask containing 40 mL of acetonitrile. A solvent-refluxing reaction was carried out at 130° C. with stirring and flowing nitrogen gas overnight. After reaction, the solution was centrifuged and the supernatant was decanted. The precipitate was washed with degassed hot water (~80° C.) three times. 2 mL of 12 wt % sodium borohydride ($NaBH_4$) solution in aqueous 14M NaOH was added to the product dispersed in 10 mL of deionized water then the mixture solution was sonicated for 10 min. A sufficient volume of 1M HCl solution was added to the solution to give a final pH of 1. The solution was centrifuged and the supernatant decanted. The precipitate was rinsed multiple times with deionized water and dried to give a final product. The C:O:S ratio of the product was 0.455:1:0.032 from X-ray photoelectron spectroscopy (XPS) results.

Example 18

Figure 8:
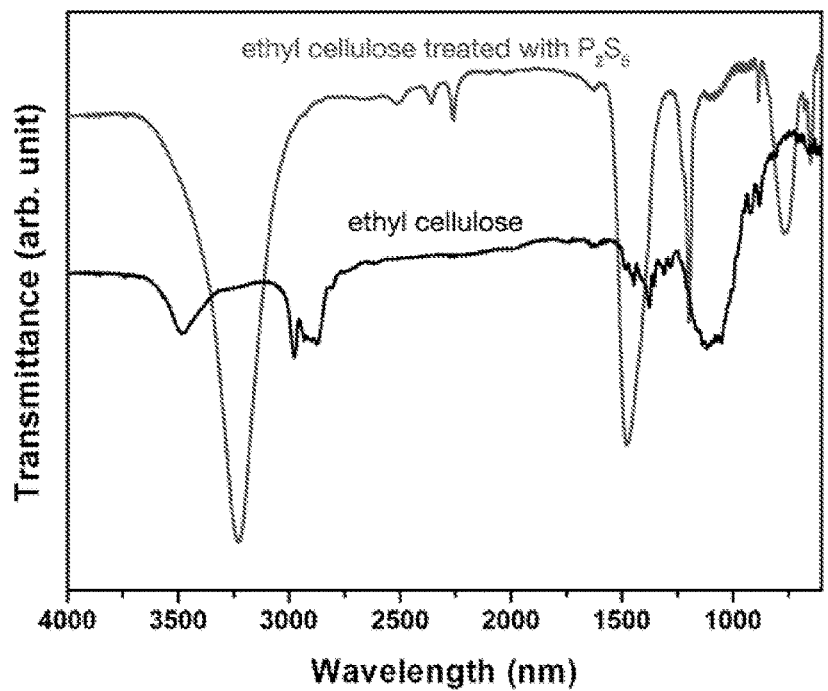
FIG. 8 shows Fourier transform Infrared (FT-IR) spectra of ethyl cellulose and the final product of Example 18.

0.2543 g of ethyl cellulose (Sigma-Aldrich, 48% ethoxyl (2.25-2.58 mol ethyl per mol cellulose)) and 0.5451 g of $P_2S_5$ powder were added to a round bottomed-flask containing 40 mL of acetonitrile. A solvent-refluxing reaction was carried out at 130° C. with stirring and flowing nitrogen gas overnight. After reaction, the solution was centrifuged and the supernatant was decanted. The precipitate was washed with degassed hot water (~80° C.) three times. 2 mL of 12 wt % sodium borohydride ($NaBH_4$) solution in aqueous 14M NaOH was added to the product dispersed in 10 mL of deionized water then the mixture solution was sonicated for 10 min. A sufficient volume of 1M HCl solution was added to the solution to give a final pH of about 1. The solution was centrifuged and the supernatant decanted. The precipitate was rinsed multiple times with deionized water and dried to give a final product. The C:O:S ratio of the product was 0.200:1:0.050 from X-ray photoelectron spectroscopy (XPS) results. FIG. 8 shows Fourier transform Infrared (FT-IR) spectra of ethyl cellulose and the final product. The spectrum of the final product exhibits a peak around 2520 $cm^{-1}$ which is assigned to a SH stretching vibration. The OH stretching at 3850 $cm^{-1}$ of ethyl cellulose was shifted to ~3225 $cm^{-1}$, assigned as a polymeric OH stretch, after the process.

Example 19

About 3 ml of graphene oxide (GO) (0.1 wt %, pH~1) was deposited on a microscope slide glass substrate by a drop casting method and dried in a lab oven at 110° C. for 1 hour subsequently. 1.26 mg of amorphous boron powder and 8.02 mg of sulfur powder were mixed until it became homogeneous by visual inspection. The GO deposited microscope slide glass and the amorphous boron and sulfur powder mixture were placed in a silica tube (11 mm I.D.). After the silica tube was evacuated and flamed-sealed, the silica ampule was gradually heated at 100° C./hr to 500° C., kept for 10 hrs, and radiatively cooled to room temperature. After the reaction, the silica ampule was intact, and there was no visible indication of corrosion on the inner surface. The microscope slide glass was taken out after breaking the silica ampule, repeatedly washed with degassed hot water (~80° C.) and finally was dried in a lab oven. The dried coating was electrically conductive.

Example 20

Figure 9A:
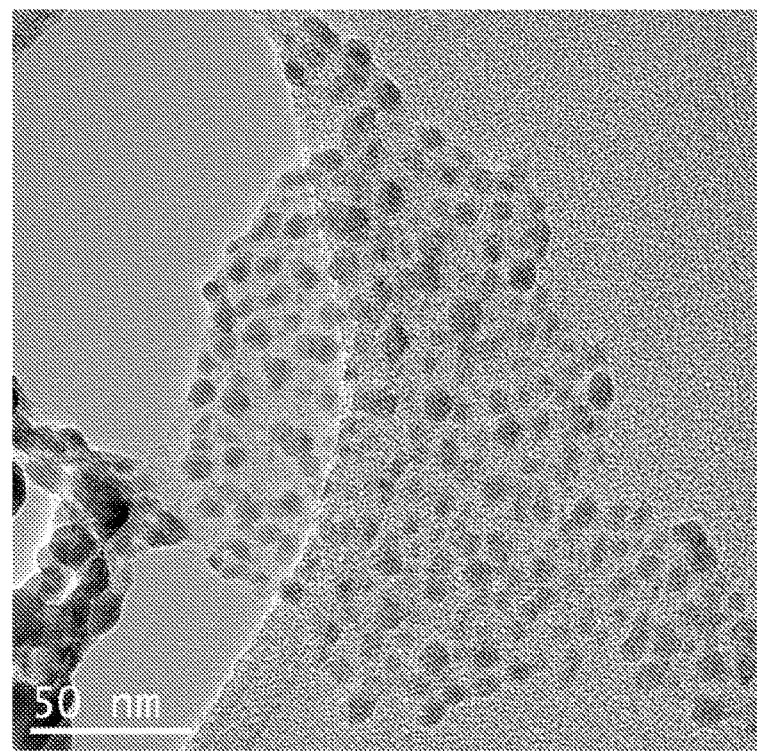
FIGS. 9A and 9B show transmission electron microscopy (TEM) images of the final product of Example 20.
Figure 9B:
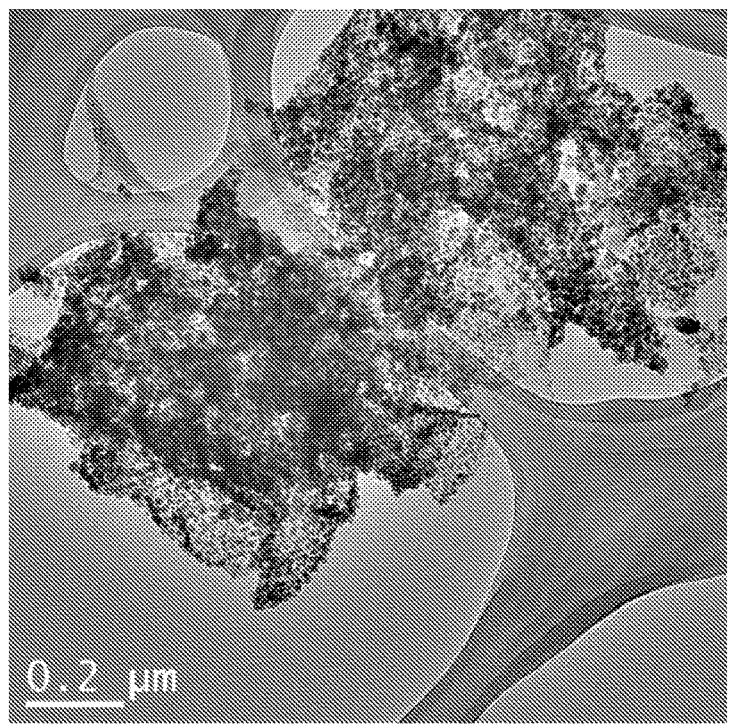

After purification, the product from Example 2 was washed with N,N-dimethylformamide (DMF) three times and then the product dispersed in DMF was sonicated for 1 hour and centrifuged at 4000 rpm for 10 min subsequently. The supernatant solution (~10 ml) was collected. About 5 mg of $CF_3SO_3Ag$ (silver trifluromethanesulfate; silver triflate) dissolved in about 10 ml of DMF was added to the supernatant solution. The product in the DMF solution was precipitated out. FIGS. 9A and 9B show transmission electron microscopy (TEM) images of the product which indicate that silver nanoparticles were well attached on the product particle surfaces.

Example 21

About 0.5 g of graphene oxide (GO) dispersed in deionized water (0.1 wt %, pH~1) was mixed with 130 mL of 1M NaOH aqueous solution. The precipitate was collected after centrifugation and was subsequently freeze-dried. The dried GO was ground on a mortar and transferred into a PTFE-lined autoclave. 13 mL of pyridine and 0.560 g of $P_2S_5$ were added into the autoclave. The autoclave was sealed and heated in a lab oven at 120° C. overnight. After reaction, the product was vacuum-filtered and washed with a copious amount of deionized water and ethanol. The washed product was dried at room temperature. The C:O:S ratios of the product were 9.65:1:0.7 from X-ray photoelectron spectroscopy (XPS) results.

Example 22

About 0.5 g of graphene oxide (GO) dispersed in deionized water (0.1 wt %, pH~1) was mixed with 130 mL of 1M NaOH aqueous solution. The solution was centrifuged and the supernatant was decanted. The precipitate was collected after centrifugation and was subsequently freeze-dried. The dried GO was ground on a mortar and transferred into a PTFE-lined autoclave. 13 mL of pyridine and 0.560 g of $P_2S_5$ were added into the autoclave. The autoclave was sealed and heated in a lab oven at 150° C. overnight. After reaction, the product was vacuum-filtered and washed with a copious amount of deionized water and ethanol. The washed product was dried at room temperature. The C:O:S atomic ratios of the product were 10:1:0.9 from X-ray photoelectron spectroscopy (XPS) results.

Example 23

About 0.5 g of graphene oxide (GO) dispersed in deionized water (0.1 wt %, pH~1) was mixed with 130 mL of 1M NaOH aqueous solution. The solution was centrifuged and the supernatant was decanted. The precipitate was washed with water to adjust pH around 9 by centrifugation. In order to obtain dried GO, freeze-drying was performed. The dried GO was ground on a mortar and transferred to 23 mL PTFE-lined autoclave. 13 mL of pyridine and 0.560 g of $P_2S_5$ were added into the autoclave. The autoclave was sealed and heated in a lab oven at 180° C. overnight. After reaction, the product was vacuum-filtered and washed with a copious amount of deionized water and ethanol. The washed product was dried at room temperature. The C:O:S atomic ratios of the product were 13.7:1:1.23 from X-ray photoelectron spectroscopy (XPS) results.

Example 24

About 0.2 g of graphene oxide (GO) dispersed in deionized water (0.1 wt %, pH~1) was homogenized for an hour at 10,000 rpm and subsequently was mixed with 130 mL of a 1M NaOH aqueous solution. The mixture solution was centrifuged and the supernatant was decanted to give a final pH around 9. The wet precipitate was centrifuged and washed with pyridine several times until the water content in the wet precipitate became around 0.02 vol %. Pyridine was then added to the precipitate to give a total volume of 37 mL. The mixture was homogenized for 2 min and transferred to a PTFE-lined autoclave. Subsequently, 0.7406 g of $P_2S_5$ powder was added to the autoclave. The autoclave was sealed and heated in a lab oven at 120° C. overnight. After reaction, the product was vacuum-filtered and washed with a copious amount of deionized water and ethanol. The washed product was dried at room temperature. The C:O:S atomic ratios of the product were 12.1:1:0.67 from X-ray photoelectron spectroscopy (XPS) analysis.

Example 25

About 0.2 g of graphene oxide (GO) dispersed in deionized water (0.1 wt %, pH~1) was homogenized for an hour at 10,000 rpm and subsequently was mixed with 130 mL of a 1M NaOH aqueous solution. The mixture solution was centrifuged and the supernatant was decanted to give a final pH around 9. The wet precipitate was centrifuged and washed with pyridine several times until the water content in the wet precipitate became around 0.02 vol %. Pyridine was then added to the precipitate to give a total volume of 37 mL. The mixture was homogenized for 2 min and transferred to a PTFE-lined autoclave. Subsequently, 0.7406 g of $P_2S_5$ powder was added to the autoclave. The autoclave was sealed and heated in a lab oven at 150° C. overnight. After reaction, the product was vacuum-filtered and washed with a copious amount of deionized water and ethanol. The washed product was dried at room temperature. The C:O:S atomic ratios of the product were 12.8:1:0.85 from X-ray photoelectron spectroscopy (XPS) analysis.

Example 26

About 0.2 g of graphene oxide (GO) dispersed in deionized water (0.1 wt %, pH~1) was homogenized for an hour at 10,000 rpm and subsequently was mixed with 130 mL of a 1M NaOH aqueous solution. The mixture solution was centrifuged and the supernatant was decanted to give a final pH around 9. The wet precipitate was centrifuged and washed with pyridine several times until the water content in the wet precipitate became around 0.02 vol %. Pyridine was then added to the precipitate to give a total volume of 37 mL. The mixture was homogenized for 2 min and transferred to a PTFE-lined autoclave. Subsequently, 0.7406 g of $P_2S_5$ powder was added to the autoclave. The autoclave was sealed and heated in a lab oven at 180° C. overnight. After reaction, the product was vacuum-filtered and washed with a copious amount of deionized water and ethanol. The washed product was dried at room temperature. The C:O:S atomic ratios of the product were 14.3:1:1.34 from X-ray photoelectron spectroscopy (XPS) analysis.

Example 27

0.200 g of hydroxyl-functionalized multi-walled carbon nanotubes (Nanostructured & Amorphous Materials, Inc.; content of OH: 5.30-5.86 wt %) was loaded in a PTFE-lined autoclave containing 13 mL of pyridine. Subsequently, 0.040 g of $P_2S_5$ powder was added to the autoclave. The autoclave was sealed and heated in a lab oven at 120° C. overnight. After reaction, the product was vacuum-filtered and washed with a copious amount of deionized water and ethanol. The washed product was dried at room temperature. The C:O:S atomic ratios of the product were 45.4:1:0.36 from X-ray photoelectron spectroscopy (XPS) results.

Example 28

0.200 g of hydroxyl-functionalized multi-walled carbon nanotubes (Nanostructured & Amorphous Materials, Inc.; content of OH: 5.30-5.86 wt %) was loaded in a PTFE-lined autoclave containing 13 mL of pyridine. Subsequently, 0.040 g of $P_2S_5$ powder was added to the autoclave. The autoclave was sealed and heated in a lab oven at 160° C. overnight. After reaction, the product was vacuum-filtered and washed with a copious amount of deionized water and ethanol. The washed product was dried at room temperature. The C:O:S atomic ratios of the product were 63.6:1:0.78 from X-ray photoelectron spectroscopy (XPS) results.

Example 29

0.200 g of cellulose powder (Sigma-Aldrich, type-20, 20 μm) and 0.165 g of $P_2S_5$ powder were loaded in a PTFE-lined autoclave containing 13 mL of pyridine. The autoclave was sealed and heated in a lab oven at 100° C. overnight. After reaction, the product was vacuum-filtered and washed with a copious amount of deionized water and ethanol. The washed product was dried at room temperature. The C:O:S atomic ratios of the product were 4.2:1:0.87 from energy dispersive X-ray spectrometry (EDX) results.

Example 30

0.200 g of cellulose powder (Sigma-Aldrich, type-20, 20 μm) and 0.165 g of $P_2S_5$ powder were loaded in a PTFE-lined autoclave containing 13 mL of pyridine. The autoclave was sealed and heated in a lab oven at 100° C. overnight. After reaction, the product was vacuum-filtered and washed with a copious amount of deionized water and ethanol. The washed product was dried at room temperature. The C:O:S atomic ratios of the product were 9.9:1:0.15 from energy dispersive X-ray spectrometry (EDX) results.

Example 31

Figure 10:
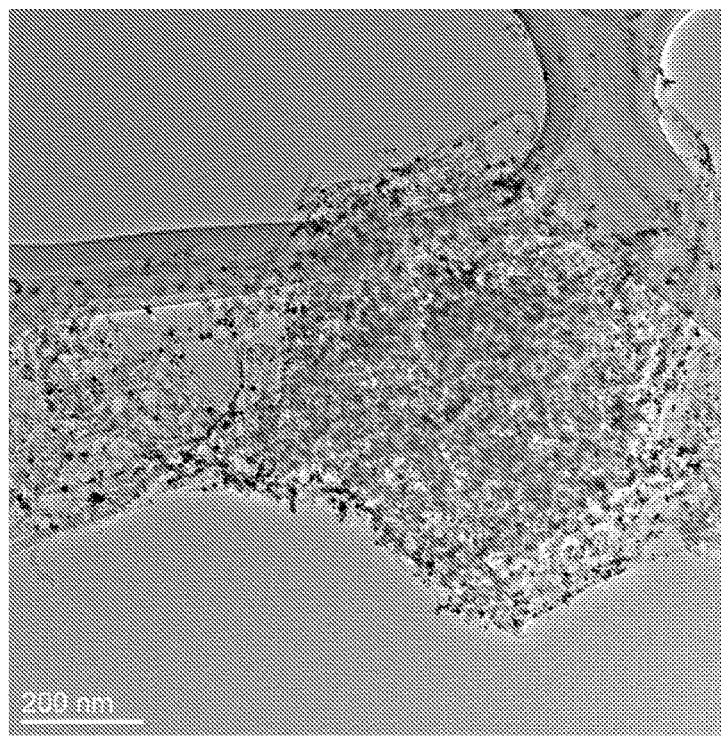
FIG. 10 shows a transmission electron microscopy (TEM) image of the final product of Example 31.

After purification, the product from Example 28 was mixed with an Au nanoparticle solution. The color of the Au nano-particles solution is red but the red color was completely disappeared within 10 seconds after the mixing. After reaction, the product was vacuum-filtered and washed with a copious amount of deionized water. The washed product was dried at room temperature. FIG. 10 shows a transmission electron microscopy (TEM) image of the product which indicates that the carbon nanotubes are decorated with gold nanoparticles.

Example 32

Figure 11:
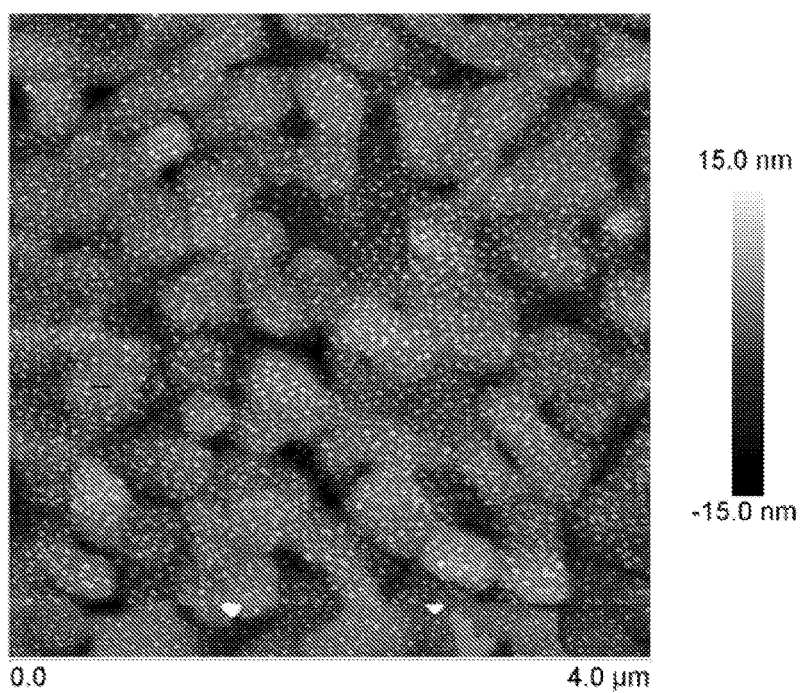
FIG. 11 shows an atomic force microscopy (AFM) image of the final product of Example 32.

The product from Example 22 was sonicated for half an hour in ethanol (200 proof) and subsequently centrifuged at 6000 rpm for 10 min. The supernatant was transferred into an Eppendorf microcentrifuge. A hydrogen flame-treated Au film (on mica) was then immersed in the solution and heated at 70° C. overnight. The Au film was taken out and washed thoroughly with 200 proof-ethanol and dried at room temperature. FIG. 11 shows an atomic force microscopic image which shows the graphene nanosheets deposited on the film.

Further modifications and alternative embodiments of various aspects will be apparent to those skilled in the art in view of this description. Accordingly, this description is to be construed as illustrative only. It is to be understood that the forms shown and described herein are to be taken as examples of embodiments. Elements and materials may be substituted for those illustrated and described herein, parts and processes may be reversed, and certain features may be utilized independently, all as would be apparent to one skilled in the art after having the benefit of this description. Changes may be made in the elements described herein without departing from the spirit and scope as described in the following claims.

What is claimed is:

1. A method of making a multifunctional composite, the method comprising:
    contacting graphene oxide with a chalcogenide compound, wherein the chalcogen is sulfur; and
    reacting the graphene oxide and the chalcogenide compound at a temperature between 120° C. and 180° C. to yield a product comprising chalcogen-containing functional groups and oxygen-containing functional groups, wherein a majority of the chalcogen-containing functional groups are thiol groups, and
    wherein the chalcogenide compound is a solid or a liquid with a boiling point greater than 50° C. at 100 kPa comprising
        at least one element selected from Groups 1, 2, and 13-16 in the periodic table,
        wherein at least one sulfur in the chalcogenide compound is not bonded to oxygen or hydrogen.

2. The method of claim 1, wherein the oxygen-containing functional groups of the graphene oxide comprise hydroxyl groups, alkoxide groups, or a combination thereof.

3. The method of claim 1, wherein the oxygen-containing functional groups of the graphene oxide are selected from the group consisting of hydroxyl groups and alkoxide groups.

4. The method of claim 1, wherein the graphene oxide is porous.

5. The method of claim 1, wherein contacting the graphene oxide with the chalcogenide compound comprises forming the chalcogenide compound in situ in the presence of the graphene oxide.

6. The method of claim 1, wherein the at least one element selected from Groups 1, 2, and 13-16 in the periodic table is not carbon.

7. The method of claim 1, wherein the chalcogenide compound comprises boron.

8. The method of claim 1, wherein the chalcogenide compound comprises phosphorus.

9. The method of claim 1, wherein contacting the graphene oxide with the chalcogenide compound comprises combining the graphene oxide and the chalcogenide compound in an inorganic medium or an organic solvent.

10. The method of claim 1, wherein contacting the graphene oxide with the chalcogenide compound comprises forming a mixture comprising the graphene oxide and the chalcogenide compound, and reacting the graphene oxide and the chalcogenide compound in an autoclave.

11. The method of claim 1, wherein contacting the graphene oxide with the chalcogenide compound comprises forming a mixture comprising the graphene oxide and the chalcogenide compound, and reacting the graphene oxide and the chalcogenide compound in a container whose atmosphere is not directly in contact with air.

12. The method of claim 1, wherein contacting the graphene oxide with the chalcogenide compound comprises forming a mixture comprising the graphene oxide and the chalcogenide compound, and reacting the graphene oxide and the chalcogenide compound under a reduced pressure, in an inert gas environment, or both.

13. A multifunctional composite formed by a process comprising:
    contacting graphene oxide with a chalcogenide compound, wherein the chalcogen is sulfur; and
    reacting the graphene oxide and the chalcogenide compound at a temperature between 120° C. and 180° C. to yield a product comprising chalcogen-containing functional groups and oxygen-containing functional groups, wherein a majority of the chalcogen-containing functional groups are thiol groups, and
    wherein the chalcogenide compound is a solid or a liquid with a boiling point greater than 50° C. at 100 kPa comprising
        at least one element selected from Groups 1, 2, and 13-16 in the periodic table,
        wherein at least one sulfur in the chalcogenide compound is not bonded to oxygen or hydrogen.

14. The product of claim 13, wherein the product is in the form of a coating, a film, a monolith, a powder, or a dispersion.

15. The product of claim 13, wherein the product is electrically conductive, thermally conductive, or both.

16. The product of claim 13, wherein the product is optically transparent or translucent.

17. The product of claim 13, wherein the product is porous or nanoporous.

18. A material comprising the product of claim 13 deposited on the surface of the material.

19. The product of claim 13, wherein the chalcogenide compound comprises $P_2S_5$.

20. The product of claim 13, wherein the chalcogenide compound comprises $P_4S_{10}$.

21. The product of claim 13, wherein the chacogenide compound comprises a complex of $P_4S_{10}$ and pyridine.

22. The product of claim 21, wherein the complex of $P_4S_{10}$ and pyridine is formed in situ.

23. The product of claim 13, wherein a ratio of sulfur atoms to oxygen atoms in the product is in a range of about 0.5 to about 1.

24. The product of claim 13, wherein a ratio of sulfur atoms to oxygen atoms in the product is in a range of about 1 to about 4.

25. The product of claim 13, wherein a ratio of carbon atoms to sulfur atoms in the product is in a range of about 5 to about 30.

26. The product of claim 25, wherein a ratio of carbon atoms to sulfur atoms in the product is in a range of about 5 to about 15.

27. The product of claim 13, wherein a ratio of carbon atoms to oxygen atoms in the product is in a range of about 10 to about 20.

* * * * *